United States Patent
Kaack et al.

(10) Patent No.: US 8,941,376 B2
(45) Date of Patent: Jan. 27, 2015

(54) METHOD FOR AUTOMATED MEASUREMENT OF THE RESIDUAL MAGNETIC FIELD STRENGTH OF MAGNETIZED FERROMAGNETIC WORKPIECES

(75) Inventors: Michael Kaack, Bochum (DE); Stefan Nitsche, Mülheim (DE); André Germes, Düsseldorf (DE)

(73) Assignee: Vallourec Deutschland GmbH, Düsseldorf (DE)

( * ) Notice: Subject to any disclaimer, the term of this patent is extended or adjusted under 35 U.S.C. 154(b) by 450 days.

(21) Appl. No.: 13/131,454

(22) PCT Filed: Nov. 18, 2009

(86) PCT No.: PCT/DE2009/001657
§ 371 (c)(1),
(2), (4) Date: Aug. 16, 2011

(87) PCT Pub. No.: WO2010/060415
PCT Pub. Date: Jun. 3, 2010

(65) Prior Publication Data
US 2012/0098532 A1    Apr. 26, 2012

(30) Foreign Application Priority Data
Nov. 27, 2008 (DE) .......................... 10 2008 059 663

(51) Int. Cl.
*G01N 27/82* (2006.01)
*G01R 33/12* (2006.01)
*G01N 27/87* (2006.01)

(52) U.S. Cl.
CPC ............ *G01R 33/1215* (2013.01); *G01N 27/87* (2013.01)

USPC .......................................... 324/238; 324/251

(58) Field of Classification Search
USPC ................................... 324/238, 251
See application file for complete search history.

(56) References Cited

U.S. PATENT DOCUMENTS 7,728,586 B2 * 6/2010 Kaack et al. ................. 324/242

FOREIGN PATENT DOCUMENTS

| DE | 2238012 A1 | 2/1974 |
| DE | 102004035174 | 2/2006 |
| GB | 2 197 958 A | 6/1988 |
| SU | 1323942 A * | 7/1987 |

OTHER PUBLICATIONS

M. Farman et al.: The origin and influence of residual magnetism on the electron beam welding of 18% Ni-maraging steels, in: Materials and Design, vol. 9, No. 5, Sep./Oct. 1988.

* cited by examiner

*Primary Examiner* — Reena Aurora
(74) *Attorney, Agent, or Firm* — Henry M. Feiereisen LLC

(57) ABSTRACT

The invention relates to a method for the automated measurement of the residual magnetic field strength of magnetized ferromagnetic workpieces, especially steel tubes, the residual magnetic field exiting the face of the tube end being measured by means of a measuring probe. Instead of directly measuring the residual field strength on the face, the curve of at least one magnetic field component is measured on the outer surface of the tube at least in the region of the tube ends and beyond the tube ends and the residual field strength on the face is inferred on the basis of the previously determined correlations between the residual field strength measured on the face and on the tube surface.

7 Claims, 2 Drawing Sheets

METHOD FOR AUTOMATED MEASUREMENT OF THE RESIDUAL MAGNETIC FIELD STRENGTH OF MAGNETIZED FERROMAGNETIC WORKPIECES

CROSS-REFERENCES TO RELATED APPLICATIONS

This application is the U.S. National Stage of International Application No. PCT/DE2009/001657, filed Nov. 18, 2009, which designated the United States and has been published as International Publication No. WO 2010/060415 and which claims the priority of German Patent Application, Serial No. 10 2008 059 663.9, filed Nov. 27, 2008, pursuant to 35 U.S.C. 119(a)-(d).

BACKGROUND OF THE INVENTION.

The invention relates to a method for automated measurement of the residual magnetic field strength of magnetized ferromagnetic workpieces, in particular of pipes made of steel.

Fault tests of steel pipes are frequently performed with magnetic methods or with magneto-inductive methods by using a magnetic bias. The test piece has then residual magnetic fields of a strength and direction that depends on the exact implementation of the test and the properties of the material. However, an undesired magnetization can also occur during pipe manufacture, during further processing and when the pipes are transported.

Residual magnetic fields can be troublesome for the further processing at the customer site and should therefore be kept as small as possible.

These residual magnetic fields are very troublesome particularly in the vicinity of the pipe ends, because the arc generated when the pipes are welded together is adversely affected by these residual magnetic fields. If the residual magnetic fields at the end face of the pipe ends are too strong, the arc is deflected, making welding difficult or even impossible.

For the aforementioned reasons, demands from customer may make it necessary to demagnetize pipe ends having a residual magnetic strength that should actually still be tolerable.

To test if the residual magnetic fields have dropped below a predetermined value, the residual magnetic fields must be measured on the pipe.

Typically, the residual magnetic fields are hereby measured at the end face of the pipe using handheld measuring devices, for example Hall probes. The use of devices for measuring magnetic fields (Gauss meter) is fundamentally known, for example, from OS 2 238 012 and is frequently used to determine the residual magnetic field on pipes. The residual magnetic field is measured by placing a calibrated Hall probe on the end face of the pipe end.

This measurement process has the disadvantage that the measurement on the end face is quite difficult to automate at reasonable costs due to structural reasons.

Sometimes, freestanding magnetic field probes are used for automatic measurements of pipes moving past the probes. However, these measurements are not very informative because a contacting measurement of the pipes would actually be required which, however, is typically omitted due to the high risk of damage by the passing pipe.

Moreover, a precisely defined distance to the end face of the pipe is very difficult to realize with moving pipes. Variations of the signals can here not be unambiguously associated with changes in the residual field strength, because these variations could also be caused by an unintentional change of the spacing between the probe and the end face of the pipe. The signal strength decreases significantly with increasing distance, which makes evaluation of the measurement results much more difficult.

SUMMARY OF THE INVENTION

It is therefore an object of the invention to provide a method for automatic measurement of the residual field strength of magnetized ferromagnetic workpieces, in particular of pipes made of steel, which can be used to determine cost-effectively, quickly, easily and reproducibly a residual field strength at the end face of a pipe.

The object is attained by a method for automatic measurement of the residual field strength of magnetized ferromagnetic workpieces, in particular of pipes made of steel, wherein the residual magnetic field exiting the end face at the pipe end is measured with a measuring probe, wherein instead of directly measuring the residual field strength at the end face, the behavior of at least one magnetic field component is measured on the exterior surface of the pipe at least in the region of the pipe ends and beyond the pipe ends, and that the residual field strength present at the end face is determined based on previously determined correlations between the residual field strength measured at the end face and on the pipe surface. Advantageous embodiments are recited in the dependent claims.

According to the teaching of the invention, instead measuring the residual field strength directly at an end face, the course of at least one magnetic field component is measured on the exterior surface of the pipe at least in a region of the pipe ends or beyond the pipe ends, and the residual field strength existing on the end face is derived based on previously determined correlations between the residual field strength measured at the end face and the residual field strength measured on the pipe surface.

According to this method, an actual measurement is initially performed at the end face and at the pipe surface of test pipes, whereafter a correlation is derived by computation.

This computed correlation is then applied during the actual test of the pipes from production, so that the residual field strength at the end face can be deduced from a measurement on the pipe surface, without performing an actual measurement at the end face.

The residual field strength at the end face of the pipe can then be calculated based on these measured values, for example, by using previously determined correlation curves stored in a computer system.

Advantageously, using the proposed method, the residual field strength on the surface of the pipe can be automatically measured in a very cost-effective and simple manner. The method can also be very easily incorporated in the structure, because the measurements can be readily performed while the pipe is transported, for example, by using stationary measurement probes arranged about the pipe surface.

Potential damage of the measurement probes during the pipe transport can be reliably prevented by setting a defined distance to the pipe surface.

The results are deducible and therefore very meaningful due to the previously set, predefined distance to the pipe surface. However, the probes must be precisely guided of before and after the pipe.

For evaluating the field strength signals, it has proven to be necessary to perform the measurement beyond the pipe end, because the signals undergo characteristic changes at that location which can be effectively used in the evaluation.

In an advantageous embodiment of the invention, the accuracy can be further improved by not limiting the measurement and evaluation to a single magnetic field component; instead, two components are used, in particular the radial and axial component.

In this embodiment, the measurement is performed using two separate measurement probes. Although it would be fundamentally feasible to evaluate the circumferential component of the field strength of the magnetic field, it has been observed that the circumferential component lacks—unlike the radial and axial component—sufficient signal characteristics that can be evaluated.

It has proven to be advantageous to use for evaluating the signals the temporal dependence of the respective maximum value and, if necessary, additionally the characteristic curve shape of the measurement values as a whole.

If additionally applied external fields, for example from an existing demagnetizing coil, can be expected during the measurement, then these effects can be advantageously be eliminated by using suitable shielding and analog or digital filters in the signal path.

Although the method of the invention was developed in particular for automatic measurement of the residual field strength at the ends of pipes, the method is fundamentally also suitable for any other type of ferromagnetic workpieces having similar problems for an end face measurement, such as metal sheets.

Additional features, advantages and details of the invention can be inferred from the following description of the illustrated figures.

BRIEF DESCRIPTION OF THE DRAWINGS

It is shown in.

DETAILED DESCRIPTION OF THE PREFERRED EMBODIMENTS

Figure 1:
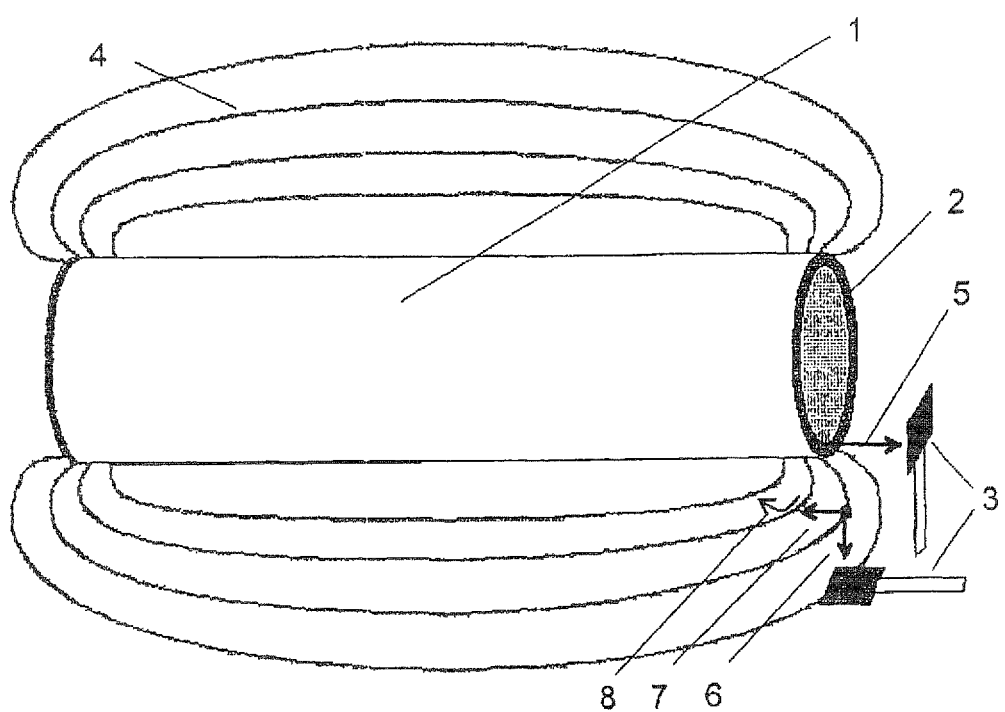
FIG. 1 a schematic diagram of an embodiment of the measurement method according to the invention for measuring the residual magnetic field strength on the pipe surface, and FIG. 2 a printout of the different components of the residual magnetic field strength.

FIG. 1 shows in a schematic diagram an embodiment of the measurement method according to the invention for measuring the residual magnetic field strength on the pipe surface.

A pipe 1 has a residual magnetic field 4, which exits from the end face 2 of the pipe as an axially oriented magnetic field 5, wherein the axially oriented magnetic field 5 can according to the state-of-the-art in typical situations only be measured manually.

Because it is difficult to accurately measure the magnetic field at the end face during the pipe transport, the measurement according to the invention is now performed on the exterior pipe surface.

The measuring probe 3 is hereby arranged at a fixed location and at a defined distance from the exterior surface of the pipe 1, so that the residual magnetic field strength of the pipe 1 can be easily measured automatically over the entire pipe length also during transport, for example via a roller bed.

FIG. 1 also shows that the magnetic field lines of the residual magnetic field 4 do not only exit from the end face of the pipe in an axial direction, but extend therefrom in the shape of an arc to the other end. According to the invention, the magnetic field lines which can be divided into a radial 6, an axial 7 and a circumferential component 8 are separately measured at a distance from the exterior pipe surface and evaluated.

The residual field strength at the end face can subsequently be deduced from correlation measurements between the residual field strength measured at the end face and the field strengths of the individual components measured on the exterior surface of the pipe 1.

Based on the measured residual field strengths, the residual field strength at the end face of the pipe can be calculated in a simple manner, for example with the help of previously determined correlations curves stored in a computer system.

Advantageously, measurements are performed for different pipe diameters and materials and the values are stored in a database.

Figure 2:
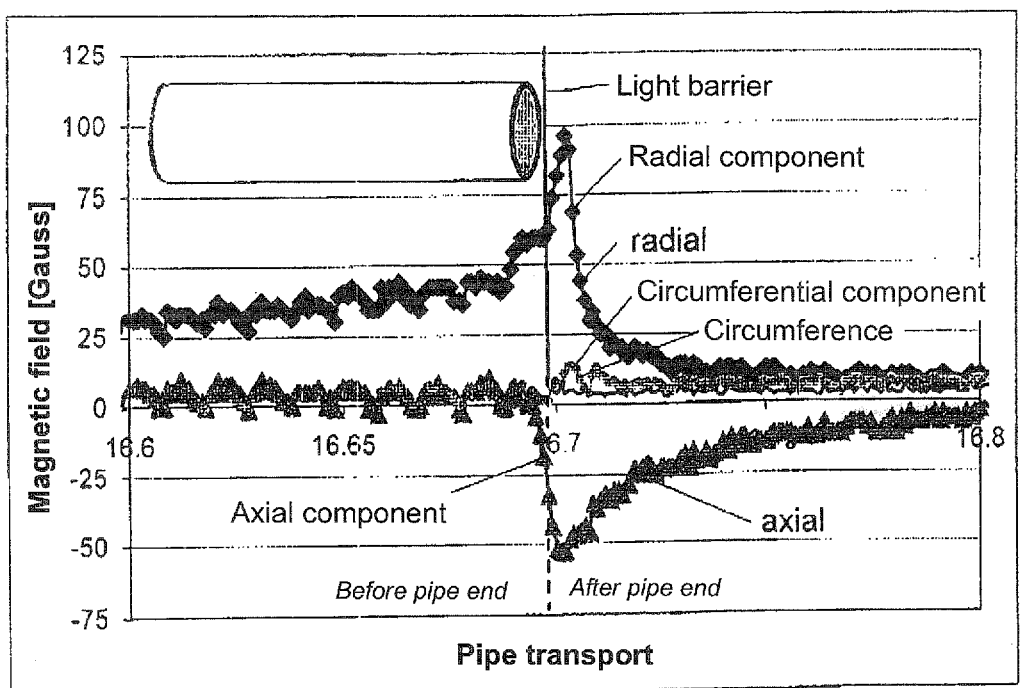

FIG. 2 shows a printout of the signal shape of the various components of the magnetic field strength. As can be seen, significant contributions to the magnetic fields on the exterior surface of the pipe can only be detected after the light barrier signal, i.e., after the pipe end and before the pipe start, respectively. The probes must therefore also be precisely guided at these locations.

The measurement curves exhibit certain characteristics, in particular a step in the radial and the axial component at the end of the pipe which can be used in the evaluation. Conversely, the circumferential component of the magnetic field strength does not have any features that could be evaluated and is therefore not included.

The invention claimed is:

1. A method for measurement of a residual field strength of an elongated magnetized ferromagnetic workpiece having at least one end, comprising the steps of:

providing an elongated ferromagnetic test piece having a residual magnetic field strength, said test piece defined by a pipe diameter and a material characteristic, placing a magnetic measuring sensor in direct contact with an end face of the test piece and measuring in a first measurement the residual magnetic field strength directly on the end face, and further separately measuring in a second measurement an axial component, a radial component and a circumferential component of the residual magnetic field strength with the magnetic measuring sensor or with another magnetic measuring sensor at a plurality of defined positions located radially outwardly from an exterior surface of the test piece distal from the end face, correlating the residual magnetic field strength of the first measurement to the axial, radial and circumferential components of the residual magnetic field strength of the second measurement at the plurality of defined positions to determine a correlation curve between the first and second measurements, repeating the first and second measurements for test pieces having different pipe diameters and material characteristics and storing the correlation curves determined therefor in a database, measuring with the magnetic measuring sensor or with the other magnetic measuring sensor at least one of the axial and the radial magnetic field component at a plurality of defined positions located radially outwardly from an exterior surface of a workpiece at least in a region of at least one end of the workpiece, retrieving from the database a correlation curve of the test piece having the pipe diameter and the material characteristic that correspond to the pipe diameter and the material characteristic of the workpiece, and determining from the measured at least one axial and radial magnetic field component of the workpiece and the retrieved correlation curve the residual magnetic field strength present at the end face of the workpiece.

2. The method of claim 1, wherein the test piece is a steel pipe and the workpiece is a steel pipe.

3. The method of claim 1, wherein at least one of the magnetic measuring sensor and the other magnetic measuring sensor is a Hall probe.

4. The method of claim 1, wherein both the axial and the radial magnetic field components on the workpiece are evaluated.

5. The method of claim 1, wherein a temporal dependence of a maximum value of the at least one axial and radial magnetic field component is used for evaluating the residual magnetic field strength.

6. The method of claim 1, wherein the residual magnetic field strength of the workpiece is evaluated based on a characteristic curve shape derived from the measured at least one axial and radial magnetic field component of the workpiece.

7. A method for measurement of a residual field strength of a magnetized ferromagnetic pipe, comprising the steps of:

moving a measuring probe in relation to the pipe, or the pipe in relation to the measuring probe, at least in a region of a pipe end and beyond the pipe end, said measuring probe constructed to measure at least one magnetic field component on an exterior surface of the pipe, measuring with a magnetic measuring probe at least one of an axial and a radial magnetic field component at a plurality of defined positions located radially outwardly from the exterior surface of the pipe at least in a region of the end of the workpiece, and determining from the measured at least one magnetic field component on the exterior surface of the pipe the residual magnetic field strength present at the end face of the pipe based on a previously determined correlation curve stored in a database between the residual magnetic field strength measured directly at an end face of a test pipe and the at least one magnetic field component measured on the exterior surface of the test pipe, wherein the previously determined correlation curve was determined by:

providing an elongated ferromagnetic test piece having a residual magnetic field strength, said test piece defined by a pipe diameter and a material characteristic, placing a magnetic measuring sensor in direct contact with an end face of the test piece and measuring in a first measurement the residual magnetic field strength directly on the end face, and further separately measuring in a second measurement an axial component, a radial component and a circumferential component of the residual magnetic field strength with the magnetic measuring sensor or with another magnetic measuring sensor at a plurality of defined positions located radially outwardly from an exterior surface of the test piece distal from the end face, determining a correlation curve for the test piece by correlating the residual magnetic field strength of the first measurement to the axial, radial and circumferential components of the residual magnetic field strength of the second measurement at the plurality of defined positions, repeating the first and second measurements for additional test pieces having different pipe diameters and material characteristics and storing additional correlation curves determined therefor in the database.

* * * * *